United States Patent
Kerrigan et al.

(10) Patent No.: US 8,084,244 B2
(45) Date of Patent: Dec. 27, 2011

(54) HYBRID MUSHROOM STRAIN J9277 AND ITS DESCENDANTS

(75) Inventors: Richard W. Kerrigan, Kittanning, PA (US); Jeffrey W. Smathers, Kittanning, PA (US); Mark P. Wach, Allison Park, PA (US)

(73) Assignee: Sylvan America, Inc., Kittanning, PA (US)

( * ) Notice: Subject to any disclaimer, the term of this patent is extended or adjusted under 35 U.S.C. 154(b) by 1443 days.

(21) Appl. No.: 11/433,178

(22) Filed: May 12, 2006

(65) Prior Publication Data

US 2008/0182321 A1 Jul. 31, 2008

Related U.S. Application Data

(60) Provisional application No. 60/680,774, filed on May 13, 2005, provisional application No. 60/682,189, filed on May 17, 2005.

(51) Int. Cl.
*A01G 1/04* (2006.01)
*A01H 15/00* (2006.01)
*C12N 1/00* (2006.01)

(52) U.S. Cl. ............ 435/254.1; 47/1.1; 800/297

(58) Field of Classification Search .............. None
See application file for complete search history.

(56) References Cited

U.S. PATENT DOCUMENTS

2004/0144020 A1 * 7/2004 Kerrigan et al. .............. 47/1.1

OTHER PUBLICATIONS

Xi Chen, Michelle Stone, Carl Schlagnhaufer and C. Peter Romaine—A Fruiting Body Tissue Method for Efficient *Agrobacterium*-Mediated Transformation of *Agaricus bisporus*; Apr. 28, 2000, pp. 4510-4513.

Philippe Callac, Frederic Moquet, Micheline Imbernon, Maria Ramos Guedes-Lafargue, Michelle Mamoun and Jean-Marc Olivier—Evidence for PPCI, a Determinant of the Pilei-Pellis Color of *Agaricus bisporus* Fruitbodies; Jan. 14, 1998, pp. 181-188.

Richard W. Kerrigan and Ian K. Ross—Allozymes of a Wild *Agaricus bisporus* Population: New Alleles, New Genotypes; 1989, pp. 433-443.

R.W. Kerrigan, D.B. Carvalho, P.A. Horgen, J.B. Anderson—The indigenous coastal California population of the mushroom *Agaricus bisporus*, a cultivated species, may be at risk of extinction; 1998, pp. 35-45.

Anton S. M. Sonnenberg, I.P.J. Van Kempen & L.J.L.D. van Griensven—Detection of *Agaricus bisporus* viral dsRNAs in pure cultures, spawn and spawn-run compost by RT-PCR; 1995, pp. 587-594.

Richard W. Kerrigan, John C. Royer, Lisa M. Bailer, Yatika Kohli, Paul A. Horgen and James B. Anderson—Meiotic Behavior and Linkage Relationships in the Secondarily Homothallic Fungus *Agaricus bisporus*; Oct. 14, 1992, pp. 225-236.

Micheline Imbernon, Philippe Callac, Patrick Gasqui, Richard W. Kerrigan, Anthony J. Velcko, Jr.—BSN, the primary determinant of basidial spore number and reproductive mode in *Agaricus bisporus*, maps to chromosome I; May 14, 1996, pp. 749-761.

* cited by examiner

*Primary Examiner* — Debbie K Ware
(74) *Attorney, Agent, or Firm* — Renner, Kenner, Greive, Bobak, Taylor & Weber

(57) ABSTRACT

A novel hybrid fungus culture, designated J9277, of the mushroom species *Agaricus bisporus* produces crops of mushrooms having white, rounded, thick-fleshed caps and proportionally long stems in a relatively short interval of time. Diverse additional strains can be developed from J9277 by various means including somatic and tissue culture selection, basidiospore selection, and hybridization to other strains of *Agaricus bisporus*, and the resulting derivative strains can be screened for desirable commercial characteristics.

5 Claims, No Drawings

HYBRID MUSHROOM STRAIN J9277 AND ITS DESCENDANTS

RELATED APPLICATIONS

This application claims the benefit of U.S. Provisional Patent Application No. 60/680,774 filed May 13, 2005 and Application No. 60/682,189 filed May 17, 2005.

TECHNICAL FIELD

This invention relates to a novel class of hybrid cultures of the edible, cultivated mushroom fungus *Agaricus bisporus* (Lange) Imbach. More particularly, this invention relates to a newly developed hybrid strain designated J9277 and to cultures that are descended or developed, either in entirety or jointly as hybrids with various strains of *Agaricus bisporus*, from J9277.

BACKGROUND OF THE INVENTION

The edible mushroom *Agaricus bisporus* (Lange) Imbach var. *bisporus*, a basidiomycete fungus, is widely cultivated around the world. In Europe and North America, it is the most widely cultivated mushroom species. The value of the annual *Agaricus bisporus* mushroom crop in the United States was about $920,000,000 in 2003-2004, according to the National Agricultural Statistics Service, Agricultural Statistics Board, U.S. Department of Agriculture (Aug. 16, 2004). More than 90 percent of the *Agaricus* mushrooms cultivated in the United States, Europe, and elsewhere have a white pileus color, in accordance with consumer preferences.

Approximately 25 years ago, the first two white hybrid strains of *A. bisporus*, developed by a laboratory at Horst, the Netherlands, were introduced into commercial cultivation. These two "Horst" strains, called U1 and U3, are closely related crosses between two pre-existing white cultivated strains, as per M. Imbernon et al., *Mycologia*, 88(5), 749-761 (1996), herein incorporated by reference. The U1 and U3 strains, while still cultivated at present, are additionally thought to be the direct progenitors of all other white *A. bisporus* mushrooms currently cultivated in most regions of the world. Commercial mushroom strains developed from U1 and U3, such as A15 and S130, are all either clones or quasi-clones of U1 or U3, being developed either by clonal vegetative propagation or from spores which retain the great majority of the parental genotype, as shown by R. W. Kerrigan et al. in *Genetics*, 133, 225-236 (1993), herein incorporated by reference. A group of strains developed either by cloning or by spore propagation, or both, from a single progenitor (as opposed to outcrossing between two different progenitors) is called a lineage group. Except for minor acquired genetic differences all white strains developed within the Horst U1 lineage group and Horst U3 lineage group share a single basic genotype with the original U1 or U3 strains, respectively (which are themselves very similar, due to their close relationship). For these reasons, and the fact that the Horst U3 lineage group is presently cultivated to a much smaller extent than the Horst U1 lineage group, modern white Agaricus mushroom cultivation is effectively a monoculture. Hence, for purposes of this disclosure, all of these cultivar strains will be described hereinafter as the "Horst U1/U3 lineage group" where both the Horst U1 lineage group and Horst U3 lineage group are implied.

Currently, the most commercially successful representative of the Horst U1/U3 lineage group is a strain designated A15 by the assignee of record. That strain, specifically, is from the Horst U1 lineage group.

The introduction of new varieties of white *Agaricus bisporus* mushrooms into commercial culture has been impeded by three difficulties. First, cross-breeding strains of *Agaricus bisporus* var. *bisporus* can be difficult and cumbersome. U.S. Pat. No. 5,304,721 sets forth many of the problems associated with cross-breeding. Second, experience indicates that most wild germ plasm resources for this species exhibit various traits that would be unacceptable in the marketplace. Third, most of these germ plasm resources incorporate alleles that give rise to brown mushrooms, which are in less demand by consumers than are white mushrooms. Color is predominately determined by alleles at the Ppc-1 locus; see P. Callac et al., *Fungal Genetics and Biology*, 23(2): 181-188 (1996), herein incorporated by reference. Alleles providing the white color trait are rare to relatively uncommon in most wild populations of *A. bisporus*. Of approximately 150 wild *Agaricus bisporus* mushroom strains collected in coastal California, only 2 were white, while the rest were brown, as seen in, inter alia, R. W. Kerrigan and I. K. Ross, *Mycologia*, 81(3):433-443 (1989), R. W. Kerrigan et al., *Molecular Ecology*, 7:35-45 (1999), herein incorporated by reference.

The difficult nature of breeding a commercially successful hybrid variety of *A. bisporus* is illustrated by the fact that very few patent applications for novel hybrid *Agaricus bisporus* strains have been filed in the United States; of these, only one (i.e., assignee of record's brown hybrid strain X618, marketed as S600) enjoyed even moderate commercial success. It is believed that no novel hybrid white mushrooms other than U1 and U3 have heretofore ever been successfully introduced into commerce in the United States.

There is a wide range of potential benefits to introducing greater diversity of strains into commercial cultivation. Novel strains may exhibit novel patterns of nutritional resource utilization, different responses to environmental manipulation, precocity or different developmental schedules, and novel aesthetic and culinary properties for the consumer. Examples of traits favored by the consumer could include a more attractive shape (i.e., more round) or a greater development of pileus tissue (i.e., greater "meatiness" or thickness). Some of these benefits may become apparent only after years of cultivation and marketing experience, for example, if a novel crop pathogen emerges. New strains may offer improved resistance to known and emerging diseases of the crop; in particular they are very likely to be much less susceptible to infection by established viral diseases that are transmitted by anastomosis (i.e., the fusion of fungal cells, called hyphae). For a more detailed description of anastomosis and of some viral diseases to which basidiomycete fungi are susceptible, see A. S. M. Sonnenberg et al., *Mushroom Science* 14, 587-594 (1995), herein incorporated by reference.

In modern mushroom production facilities, a crop of mushrooms may typically occupy production space for 46-57 days, between the planting of spawn in the compost and the emptying and cleaning of the facility to prepare for the initiation of the next crop. During that crop cycle, three 'flushes' of mushrooms are normally harvested at about weekly intervals. In some cases, the scheduling of new crop production cycles may lead to the disposal of the prior crop before three full flushes of mushrooms can be obtained. There are three potential opportunities for accelerating this crop cycle: (1) during the spawn run interval, typically of 13-16 days duration, (2) during the case run interval, typically of 15-19 days duration, and (3) during the flushing/harvest periods, typically of 18-22 days duration. There are several economic benefits that derive from a shorter crop cycle: (a) higher utilization of physical plant, and distribution of overhead costs over more crops, (b) ability to routinely complete harvest of the third flush, increasing productivity, (c) opportunity to harvest more of the crop earlier with respect to disease pressure, which impacts crop quality and value, and (d) additional scheduling flexibility represented by multiple strain-schedule options.

In some markets, mechanical harvesting is preferred due to the higher cost of human labor. In order for a mushroom crop to be suitable for mechanical harvesting, uniform development and a sufficiently long stem are necessary and desirable.

SUMMARY OF THE INVENTION

Broadly, the present invention is directed to a new and distinct class of *Agaricus bisporus* mushroom cultures comprising the newly developed hybrid strain J9277 and strains developed or descended from it. Thus, the present invention encompasses J9277, and all strains developed from it by any means, including but not limited to single-spore cultures, multi-spore cultures, and somatic selections, and also all hybrid cultures descended from J9277, including first generation hybrid cultures and any further hybrid cultures produced by the descendents of J9277. In a more preferred embodiment of the invention, the J9277 strain, or strains descended therefrom, may be crossed with a strain of, or a strain descended from, the Horst U1/U3 lineage group to form additional distinct novel hybrid cultures.

The advantages of the present invention over existing prior art relating to *Agaricus bisporus* mushrooms and cultures, which shall become apparent from the description which follows, are accomplished by the invention as hereinafter described and claimed.

One or more aspects of the present invention may be accomplished by a hybrid fungus culture of *Agaricus bisporus* designated as strain J9277, a representative culture of said fungus strain having been deposited under ATCC Accession No. PTA-6692.

One or more other aspects of the present invention may be accomplished by a hybrid fungus culture of *Agaricus bisporus* produced by crossing a first culture of *Agaricus bisporus* with a second culture of *Agaricus bisporus*, wherein at least one of said first and said second cultures of *Agaricus bisporus* is a fungus strain designated J9277 or a fungus strain descended or developed from said strain J9277.

One or more other aspects of the present invention may be accomplished by a culture of *Agaricus bisporus* produced by selection of somatic subcultures (including protoplast regenerants), basidimatal tissue explants, single basidiospores, or multiple basidiospores, from the culture of hybrid fungus culture of *Agaricus bisporus* designated as strain J9277 or a culture descended or developed from strain J9277.

Advantageously, it has been found that the hybrid culture J9277 produced as the present invention exhibits commercially acceptable physical and performance characteristics. For example, J9277 has a white cap. J9277 can produce a crop of mushrooms several days earlier than existing commercial strains such as A15. J9277 can produce a longer-stemmed mushroom, relative to commercial strains like A15, that is preferred for mechanical harvesting systems. J9277 has thicker cap flesh, relative to the width of the cap, and therefore a meatier aspect, than the commercial strain A15. J9277 also has a rounder cap shape than A15.

It has also been found that J9277 can produce hybrid descendents by making crosses with J9277 to other strains of *Agaricus bisporus*. Brown hybrid descendents of J9277 can be produced by making crosses to other strains carrying an allele for the brown color at the Ppc-1 locus.

PREFERRED EMBODIMENT FOR CARRYING OUT THE INVENTION

As noted hereinabove, the present invention relates to cultures of the hybrid *Agaricus bisporus* strain J9277, to cultures developed from J9277 directly, and to cultures that are descendents of J9277 produced via hybridization of either the J9277 strain itself, or strains developed from the J9277 strain, to a second strain of the species. It will be understood that the term "descended" is specifically intended to mean genealogically descended from the strain rather than evolutionary descent, i.e., a naturally occurring process of genetic divergence typically involving at least hundreds of generations and thousands of years. It will be further understood that the term "developed from" is meant to include any means of selection or manipulation of any element of the starting material, in this case a mushroom culture of *Agaricus bisporus*. Also, it will be understood that the terms "strain," "culture," and "variety" can be used essentially interchangeably for this invention, but attempts have been made to maintain a distinction between the terms based on context. For purposes of this invention, "strain" has been generally used when discussing the more abstract, genealogical composition of matter; "culture" has been generally used when discussing the actual physical embodiment of the composition of matter to be grown typically on a sterile medium; and "var." (i.e. "variety") has been generally used when discussing the particular taxonomic variety of *Agaricus bisporus*. The term "variety," as used in many U.S. plant patents, is essentially equivalent to "strain."

Hybridization of *Agaricus bisporus* cultures of the invention may be accomplished by allowing two different cultures, one of which is strain J9277 or a strain descended from the strain J9277, to grow together in close proximity, preferably on sterile media, until anastomosis (i.e., hyphal or cell fusion) occurs. Where two compatible nuclei (i.e., two nuclei carrying different alleles at the Mat locus, which determines mating type) are present in a fusion cell, they jointly proliferate and establish a growing heterokaryotic culture. This process is commonly known as crossing. Where each of the two nuclei in the resulting heterokaryotic culture was contributed by a different parental strain participating in the fusion process, then the new heterokaryon is a first-generation outcrossed hybrid offspring of the two parents. That is, where the J9277 strain is one of the parental strains and is crossed with another parental strain of *Agaricus bisporus*, the resultant hybrid is a first-generation outcrossed hybrid culture defined as one embodiment of the present invention.

Unlike homokaryons, described below, heterokaryon cultures are capable of producing mushrooms and are routinely incorporated into commercial products such as mushroom spawn and casing inoculant as described below. They can also serve as the progenitors of future generations of inbred and outcrossed descendants. Thus, the present invention provides for the crossing of strains descended from the J9277 strain as well. 'Inbred' is used broadly here to include self-fertilized heterokaryon progeny from spores of a single parent as well as offspring between a hybrid and itself or one of its own progenitors.

The preferred method of hybridization uses two haploid strains (i.e., homokaryons), one being obtained from each non-haploid (i.e., heterokaryotic) parental strain. Haploid strains, which incorporate only a single type of nucleus, hybridize with a higher frequency of success, and produce offspring with only a single, predictable, nuclear genotype, in contrast to fusions involving heterokaryons. Homokaryons may be developed from parental strains via several methods including generation of protoplasts, isolation of hyphal tips, or from germinated spores. The latter method provides homokaryons with diverse genotypes, as a result of meiotic recombination during sporogenesis. All of the foregoing methods can also be employed to develop cultures of heterokaryon selections of J9277 that can produce crops of mushrooms and accomplish various aspects of the invention.

J9277 is a fourth-generation hybrid descended from the tetrasporic brown wild parent strain JB137, which belongs to the taxonomic variety *Agaricus bisporus* var. *burnettii*, and the commercial white parent strain U1, which belongs to *Agaricus bisporus* var. *bisporus*. The first generation crosses between JB137 and U1 produced a series of brown hybrid strains; after screening these, hybrid strain J1229 was selected for further development.

In the second hybrid generation, crosses between J1229 and U1 produced a series of hybrids that were either brown or white, depending on their inherited genotype. After screening these hybrids, the second generation hybrid strain J5466 was selected for further development.

Contemporaneously, another first generation hybrid was produced from crosses between wild bisporic parent strain RWK 1634 and the white commercial parent strain known as White Queen 101. Several hybrid offspring of these crosses were screened, and hybrid strain B5069 was selected for further development.

In the third hybrid generation, parent strain J5466, which carries two white alleles, was crossed with parent strain B5069, which also carries two white alleles. A series of white hybrid strains was produced, and after screening, hybrid strain J6211 was selected for further development.

To create the fourth generation hybrid strain J9277, the homokaryon J6211-s4, obtained from hybrid parent strain J6211, was mated with homokaryon S130-d, from the Sylvan white commercial parent strain S130. The product of the successful cross was designated J9277. Crops of J9277 were produced, and a culture of J9277 was re-isolated from tissue explants from mushrooms obtained from these crops.

To create hybrid descendents of J9277, homokaryons obtained from J9277 were crossed with homokaryons from a second parent strain of *Agaricus bisporus*.

A deposit of a culture of hybrid strain J9277, as disclosed herein and recited in the appended claims, has been made under the terms of the Budapest Treaty with the American Type Culture Collection (ATCC), 10801 University Boulevard, Manassas, Va. 20110. The date of deposit was May 3, 2005. The culture deposited was taken from the same culture maintained by Sylvan America, Inc., 198 Nolte Drive, Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The ATCC Accession No. is PTA-6692. The deposit will be maintained in the depository for a period of 30 years, or 5 years after the last request, or for the effective life of the patent, whichever is longer, and will be replaced as necessary during that period. The strain J9277 will be irrevocably and without restriction or condition released to the public upon the issuance of a patent.

If not already explicit, it will further be appreciated that hydridization can further occur between two different *Agaricus bisporus* cultures wherein one of the cultures is the J9277 strain or is descended or developed from the J9277 strain. Thus, all progeny, descendents, and selections of the J9277 strain may be used in further crosses.

It will be understood that a culture of *Agaricus bisporus* will produce mushrooms (=basidiomata) only under the appropriate conditions. Those conditions necessary to produce mushrooms from such a culture are well known to those having ordinary skill in the art, and can be determined without undue experimentation. *Agaricus bisporus* mushrooms are customarily produced according to the following process, although any method known in the art for fruiting the cultures can be employed. A pure culture incorporating a single mushroom strain is clonally propagated on a sterile medium. This culture is a mycelium comprising many microscopic, thread-like elements called hyphae, which are themselves composed of cellular compartments. For commercial purposes, some of the pure culture is transferred to a larger volume of an appropriate medium which, when fully grown, can be used as inoculum to produce commercial products such as spawn and casing inoculant (technically all forms of the pure culture are inoculum in a broad sense). Mushroom spawn is usually prepared from a sterilized cooked grain such as rye, wheat, or millet, which may be amended with other materials such as chalk. Casing inoculant is typically composed of particulate matter such as peat moss, vermiculite, and/or compost, blended with some nutrients and moistened with water. A small volume of inoculum is mixed with a larger volume of sterilized grain (for spawn) or other substrate (for casing inoculant). When the pure culture mycelium has grown throughout and fully colonized the larger volume of sterilized substrate, the resulting mass of substrate plus mycelium is now a conventional commercial product, either spawn or casing inoculum.

To produce a crop of mushrooms, the mushroom farmer combines a small volume of mushroom spawn with a larger volume of pasteurized compost in a purpose built structure. Conventional compost is prepared from straw plus water, one or more nitrogen sources, and inorganic calcium sources. Preparation of compost typically takes two to three weeks, culminating in a period at elevated temperatures sufficient to kill invertebrates and many undesirable fungi and bacteria. Once spawned, about 13 to 16 days are required for the compost to become fully colonized by the mycelium. At this stage, a layer of porous, absorbent, low-nutrient material such as soil or peat moss is placed over the compost to a depth of about 2 inches. This layer, called the "casing," may preferentially incorporate casing inoculant or another source of mushroom mycelium such as colonized compost, to speed and enhance the crop. It is important to use the same strain in the spawn/compost and the casing inoculant. Development of the mushroom mycelium in the casing, and formation of mycelial strands and mushroom primordia, takes approximately 7-10 days. Subsequently the mushrooms will enlarge during the fruiting process, which requires about 7-10 days more to produce mushrooms mature enough for harvest and sale. Additional crops, called flushes or breaks, will be produced at approximately weekly intervals. Modern farmers find that taking three flushes is most profitable.

In order to demonstrate practice of the invention, a subculture of strain J9277 was propagated as described above to produce spawn and casing inoculant. This was used in a series of tests in Sylvan facilities that produced data on the desirable commercial properties of strain J9277.

It was observed regularly that crops of J9277 were ready to harvest 1 to 2.5 days earlier than commercial control strain A15. For example, in one test, in a facility that employs a relatively accelerated cropping schedule, J9277 produced a heavy crop 13 days after casing, while A15 produced a light harvest on day 14 and a moderately heavy crop on day 15. This pattern was also observed in trials at independent test sites, where a two day speed advantage for J9277 over A15 was typical.

Also observed in trials at independent test sites was the earlier readiness of J9277, relative to A15, for the application of casing material. For example, at one test site, where commercial operations use a 16-day spawn run period prior to casing for the A15 strain, best results have been obtained using a 12-day spawn run for J9277.

An additional regular observation from trials of J9277 is that the harvest of each of three flushes of mushrooms obtained from a single spawning of compost can be concluded promptly, at regular intervals. This means that the entire third flush can be reliably harvested prior to the scheduled termination of the crop, allowing maximum product harvest while maintaining the facility schedule. This is sometimes a problem with other commercial strains. The entire third flush of mushrooms produced by J9277 has typically been harvested on day (17-)18 of the harvest period.

In aggregate, J9277 can save 2-4 days in spawn run, 1-2 days from case to crop, and 0-4 days during the cropping period. A realistic net observed gain of about 7 days represents about 12-15% of the total crop turnaround time required by conventional strains, allowing a corresponding improvement in the efficiency of facility utilization. Facility scheduling can be more flexible, and a full third flush can be harvested even on a tight schedule. Accelerated cropping also allows more of the crop to be obtained under conditions of relatively lower disease pressure.

Measurements of physical dimensions of mushrooms produced by J9277 show differences from mushrooms produced by A15. Equal numbers of mushrooms of both strains, grown at the same time in the same environment and conditions, were measured. Proportional measures (ratios of two direct measurements) were calculated because absolute dimensions vary widely among mushrooms of any strain, and are influenced by cultural factors. (1) 'Cap Width' (CW) is defined here as the greatest horizontal distance between two vertical lines tangential to either side of the cap. (2) 'Cap Flesh Thickness' (CFT) is the vertical distance from the top of the lamellae (i.e., gills) adjacent to the stipe, to the surface of the pileus directly above. (3) 'Cap Fleshiness' (CF) is calculated here as CFT/CW. (4) 'Cap Height' (CH) is the vertical distance between two lines that are horizontal and tangential to the lowest and highest portions of the cap, respectively. (5) 'Cap Roundness' (CR) is calculated here as CH/CW. (6) 'Stem Length' (SL) is the distance from the bottom of the stem to the boundary between the stem and cap structures. (7) 'Proportional Stem Length' (PSL) is calculated here as SL/CW.

A t-test was used to assess the statistical significance of the observed differences. These data are summarized in TABLE I set forth hereinbelow.

TABLE I

Measurements of Mushroom Size and Shape

| Measure | Mean, J9277 | Mean, A15 | p value: t-test | J9277 vs A15 |
|---|---|---|---|---|
| Cap Width (CW) | 41.2 mm | 47.6 mm | NA | NA |
| Cap Flesh Thickness (CFT) | 12.95 mm | 13.35 mm | NA | NA |
| Cap Fleshiness (CF = CT/CW) | 0.317 | 0.283 | 0.0051 | +12.0% |
| Cap Height (CH) | 24.4 mm | 25.5 mm | NA | NA |
| Cap Roundness (CR = CH/CW) | 0.59 | 0.54 | 0.0001 | +11.0% |
| Stem Length (SL) | 39.5 mm | 41.6 mm | NA | NA |
| Pr. Stem Length (PSL = SL/CW) | 0.96 | 0.88 | (0.056) | +9.7% |

Cap Fleshiness in J9277 was about 12% greater than in A15 (p=0.0051). Mushrooms of J9277 appear to be correspondingly more 'meaty' than those of A15. This is an appealing consumer trait. Cap roundness was about 11% greater in J9277 than in A15 (p=0.0001), and this is also likely to appeal to the consumer. These differences were highly statistically significant.

In this sample, the Proportional Stem Length, or ratio of SL/CW, was about 9% greater in J9277 than in A15. This difference approached the accepted threshold of statistical significance (p=0.056). Under other cultural conditions J9277 has been observed to produce mushrooms with a greater absolute stem length (SL) in combination with a tightly closed cap, a combination that is desirable for mechanical harvesting.

To determine whether the sample size of ten mushrooms per strain had limited the power of the t-test to demonstrate the statistical significance of any difference, two measurements were repeated on a larger sample of twenty mushrooms per strain from another test crop that included treatments of both A15 and J9277. The results are presented in Table II.

TABLE II

Measurements of Mushroom Size and Shape

| Measure | Mean, J9277 | Mean, A15 | p value: t-test | J9277 vs A15 |
|---|---|---|---|---|
| Cap Width (CW) | 39.9 mm | 45.5 mm | NA | NA |
| Stem Length (SL) | 38.1 mm | 31.9 mm | 0.0007 | +19% |
| Pr. Stem Length (PSL = SL/CW) | 0.97 | 0.72 | 0.00002 | +36% |

It is evident from the direct measurements of CW and SL that conditions for the test crop that produced the mushrooms measured for Table II favored the development of a longer stem in J9277, relative to the sample reported in Table I. For PSL, J9277 had a 36% advantage over A15, and a highly significant difference in a t-test (p=0.00002). J9277 also had a 19% (=6 mm) advantage over A15 in absolute stem length (SL; p=0.0007). Although proportional measurements (=ratios) are preferred when size of the mushroom is an irrelevant source of variability, the absolute stem length is commercially and economically important. For example, mechanical harvesting favors a longer stem. From the data presented in Table II, J9277 is shown to be better suited than A15 for mechanical harvesting.

As a consequence of having wild strains JB 137 and RWK 1634 as ancestors, J9277 and all related hybrid strains belonging to the class of the invention carry distinctive genetic markers not found in the Horst U1/U3 lineage group. For example, the new hybrid variety J9277 has a novel DNA sequence in the Internal Transcribed Spacer regions (ITS1+2) of the nuclear rRNA gene gene complex. There are five relevant polymorphisms in the sequences of *Agaricus bisporus*, at positions 52, 253, 461, 522, and 563 of the nominal *A. bisporus* var. *bisporus* sequence, which is numbered from the initial 5′ 'G' (=position 1) in the sequence GGAAGGATC near the 3′ end of the 18S rRNA gene. TABLE III provides the allelic states of relevant members of the J9277 pedigree, and of the S130 member of the Horst U1/U3 lineage group.

TABLE III

ITS1 + 2 alleles of the J9277 pedigree and of S130

| Strain | Allele(s) | 52 | 253 | 461 | 522 | 563 |
|---|---|---|---|---|---|---|
| JB 137 | C + D | C | A | T | C/T | C |
| RWK 1634-s3 | A | C | G | A | C | C |
| J6211-s4 | A | C | G | A | C | C |
| S130b | E | C | G | T | T | T |
| S130d | B | T | G | T | T | T |
| J9277 | A + B | C/T | G | A/T | C/T | C/T |
| S130 | B + E | C/T | G | T | T | T |

From TABLE III it will be seen that allele A, present in ancestral homokaryon RWK 1634-s3, was inherited by J6211-s4, and subsequently by J9277. J9277 also inherited allele B from homokaryon S130d. The A+B genotype of J9277 is novel and distinct from the B+E genotype of the Horst U1/U3 lineage group, as exemplified by S130.

It would be expected, based upon averages, that about 12.5% of the nuclear genome of J9277 was inherited from the wild strain RWK 1634, and about 6.25% was inherited from the wild strain JB 137. Thus the genome of J9277 comprises a unique and novel combination of genetic material from its progenitors. The actual amounts of genetic material, in J9277, contributed by each ancestor in the first and second generations of the pedigree is difficult to determine precisely, and is expected to vary among hybrids of each subsequent generation.

From TABLE III it is clear that J9277 can be distinguished from currently marketed white-capped strains of *Agaricus bisporus* by its genotype, in addition to the other distinctive characteristics discussed hereinabove. Data presented herein is non-limiting as these are only examples of useful markers; several others have been documented. It is important to note that all hybrids belonging to the invented class will have novel genotypes due to the presence of genetic material from JB 137 and RWK 1634; however those genotypes may differ from the example of J9277 presented above. Further, in subsequent outcrossed, backcrossed, and selfed generations the proportion of genetic material and markers from J9277 may change. In selfed progeny, a heterozygous marker may become homozygous, producing the appearance of a novel genotype, whereas in actuality a nearly complete subset of the original genotype will be present. For these reasons, although genetic markers can readily identify members of the invented class, and genotypes will normally remain stable attributes of individual strains within the class, no specific genotype is represented to be an invariable attribute of the class as a whole.

In order further to demonstrate practice of the invention, four homokaryons were obtained from single spores of hybrid strain J9277. These four homokaryons were crossed with a homokaryon obtained from another strain that is a hybrid descendent of Horst U1. The 4 resulting hybrids had brown caps, demonstrating that novel traits can be introduced into descendents of J9277 via hybridization. The resulting hybrids can be evaluated for economically valuable traits as described above.

In yet a further demonstration, cells from lamellar tissue blocks of J9277 were transformed to hygromycin resistance via an *Agrobacterium tumefaciens*-facilitated protocol using the plasmid vector pBGgHg, which contains the hpt gene under the control of an *Agaricus bisporus* gpd promotor, as described in Chen et al. (2000), the disclosure of which is incorporated herein by reference. Transformed cell lines were confirmed by virtue of their ability to grow on agar media containing hygromycin, whereas the untransformed wild-type J9277 did not grow on this medium. 35 transformed cell lines were produced. One transformed J9277 cell line was used to prepare grain spawn that was used to inoculate compost. A mushroom crop with the typical behavior and appearance of J9277 was produced from the inoculated compost. A tissue culture of one of these mushrooms was generated and it maintained the hygromycin-resistant phenotype on the selective agar medium, showing that the introduced trait was stably expressed. These results demonstrate that J9277 can be used as a system for the production of heterologous proteins via DNA-mediated transformation.

Based on the foregoing disclosure, it should now be apparent that cultivation of hybrid strain J9277 to produce crops of white capped mushrooms with novel physical and genetic characteristics, more rapidly (after spawning of the compost) than crops of existing commercial white mushroom strains, will carry out the objects of the present invention. It should now be further apparent that producing novel *Agaricus bisporus* mushroom strains by enabling hybridization between hybrid strain J9277 and other strains of *Agaricus bisporus*, including those strains belonging to the Horst U1/U3 lineage group, will carry out yet other objects of the present invention.

In addition to commercially acceptable characteristics, some of these hybrid strains will have other commercially valuable characteristics, such as antagonisim to heterokaryon stains of the Horst U1/U3 group, leading to reduced susceptibility to infection with viral diseases. Hybrids belonging to this class can be produced by various means, including those disclosed above. It is to be understood that any variations evident fall within the scope of the claimed invention and thus, the selection of specific hybridization techniques and sources of homokaryons and heterokaryons can be determined without departing from the spirit of the invention herein disclosed and described. Thus, the scope of the invention shall include all modifications and variations that may fall within the scope of the attached claims.

What is claimed is:

1. A hybrid mushroom culture of *Agaricus bisporus* designated strain J9277, a representative culture of said hybrid strain J9277 having been deposited under ATCC Accession No. PTA-6692.

2. Inoculum comprising the hybrid mushroom culture of claim 1.

3. Mushroom spawn comprising the inoculum of claim 2.

4. Casing inoculant comprising the inoculum of claim 2.

5. Mushrooms produced by fruiting of the hybrid mushroom culture of claim 1.

* * * * *